US00PP29263P3

(12) United States Plant Patent
Olesen

(10) Patent No.: US PP29,263 P3
(45) Date of Patent: May 1, 2018

(54) MINIATURE ROSE PLANT NAMED 'POULPAR100'

(50) Latin Name: ***Rosa* hybrid**
Varietal Denomination: Poulpar100

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days. days.

(21) Appl. No.: 15/330,299

(22) Filed: Sep. 6, 2016

(65) Prior Publication Data

US 2018/0070506 P1 Mar. 8, 2018

(51) Int. Cl.
*A01H 5/02* (2006.01)

(52) U.S. Cl.
USPC ..... Plt./122

(58) Field of Classification Search
USPC ..... Plt./122
CPC ..... A01H 5/0222
See application file for complete search history.

(56) References Cited

PUBLICATIONS http://www.poulsenroser.com/assortment/rose-collections/parade/victory-2014.aspx; No date; 1 page.*

* cited by examiner

*Primary Examiner* — Kent L Bell

(57) ABSTRACT

A new garden rose plant of the Miniature class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poulpar100'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpar100', originated as a single seedling from the stated cross.

The new variety may be distinguished from its male pollen parent and female seed parent primarily by the following characteristics. The male pollen parent plant has near white flowers, while the new variety has red flowers. The female seed parent plant has russet colored flowers, while the new variety has red flowers.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar100' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpar100' was selected in the spring of 2012 by the inventor as a single plant from the progeny of the aforementioned hybridization.

Asexual reproduction of 'Poulpar100' by traditional budding and rooted cuttings was first done by Mogens N. Olesen in the nursery in Fredensborg, Denmark in July, 2012. This initial and other subsequent asexual propagations conducted in controlled environments have demonstrated that the characteristics of 'Poulpar100' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar100'.

Specifically illustrated in FIG. 1 are open flowers viewed from the side and above, sepals detached showing the receptacle and reproductive flower parts, and flower petals detached.

DETAILED DESCRIPTION OF THE VARIETY

Figure 1:
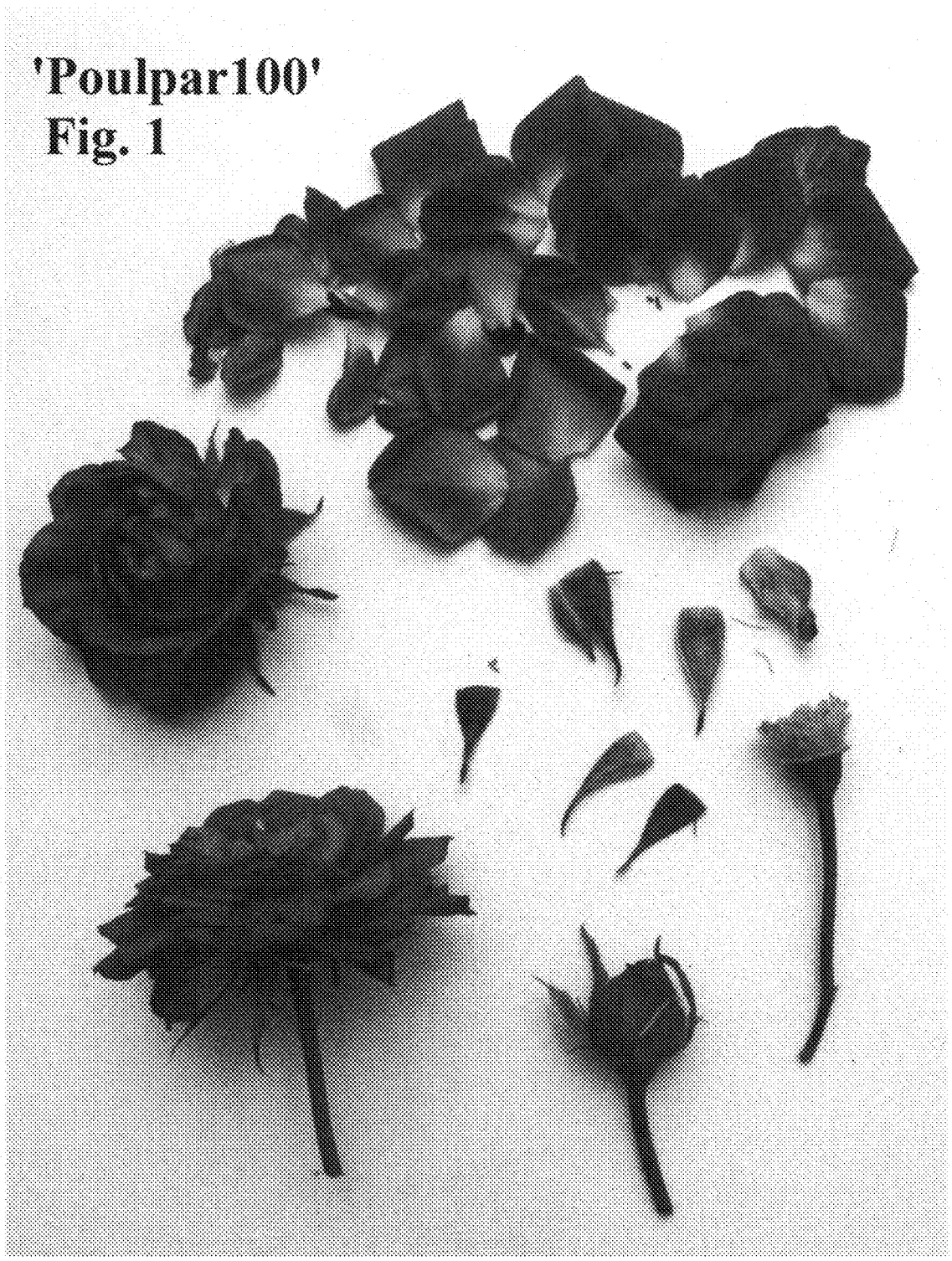
Figure 2:
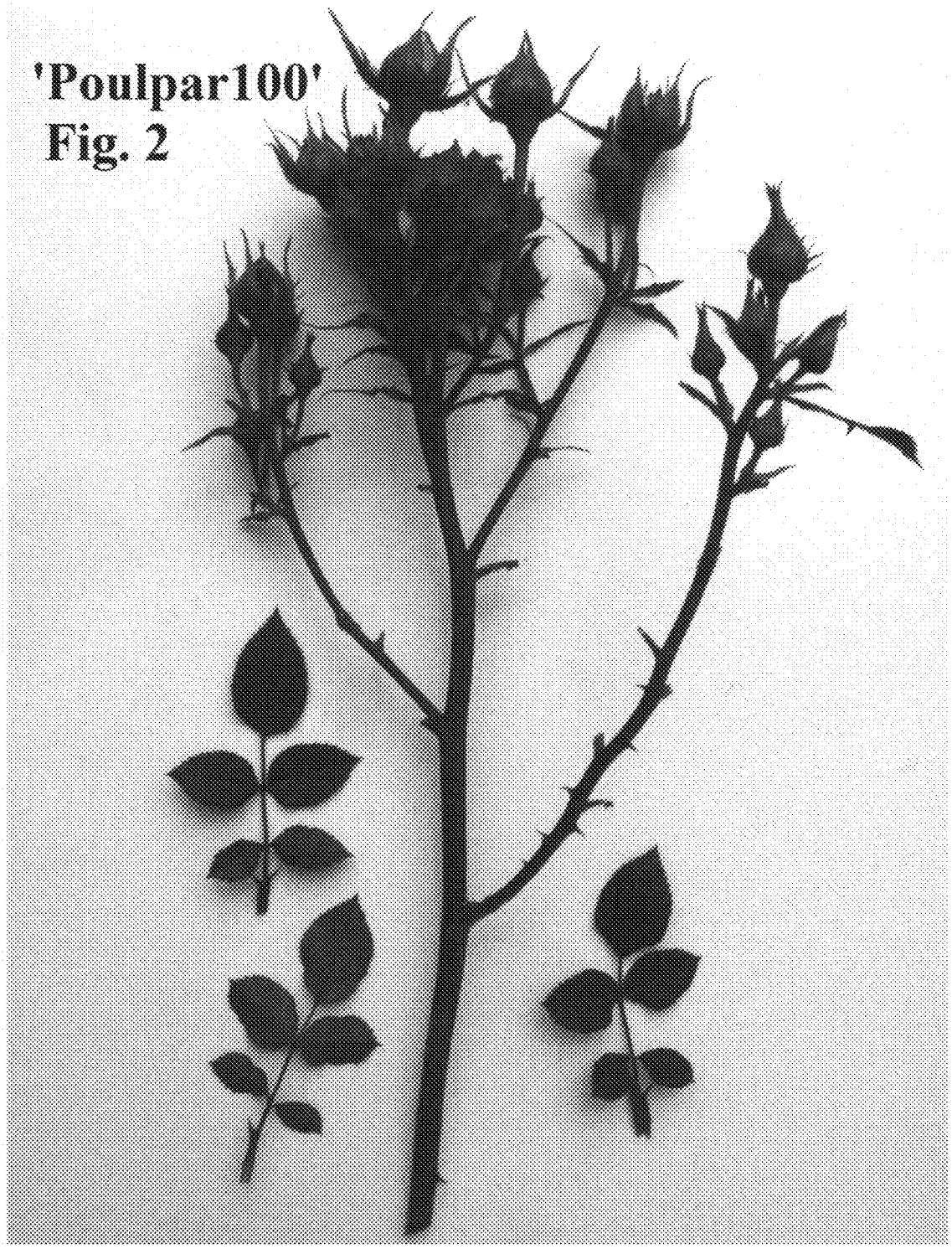
FIG. 2 shows a flowering branch with many flower buds, bare stems, and leaves. Plants shown are 2 years of age.

The following is a description of 'Poulpar100', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar029', U.S. Plant Pat. No. 16,148 are compared to 'Poulpar100' in Chart 1.

CHART 1

| | 'Poulpar100' | 'Poulpar029' |
|---|---|---|
| Petal Count | 70 | 35 |
| Flower Diameter | 50 mm | 35 mm |
| General Tonality of Flower Color | Red Group 46B | Red Group 53A |

FLOWER AND FLOWER BUD

Blooming habit: Continuous.

Flower bud:

*Size.*—Upon opening, 14 mm in length from base of receptacle to end of bud. Bud diameter is 14 mm.

*Bud form.*—Broad based ovoid.

*Bud color.*—As sepals divide petals are Orange-Red Group N34A.

*Sepal inner surface.*—Color: Yellow-Green Group 145C. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—4 mm long, 4 mm wide.

*Receptacle.*—Texture: Smooth. Size: 5 mm tall by 5 mm wide. Color: Yellow-Green Group 144A with intonations of Greyed-Red Group 178A. Shape: Campanulate.

*Pedicel.*—Surface: Smooth. Length: 30 to 35 mm. Diameter: 3 mm on average. Color: Yellow-Green Group 152D with intonations of Greyed-Red Group 178B. Strength: Strong.

*Peduncle.*—Length: 2 to 12 cm. Diameter: About 4 mm. Color: Yellow-Green Group 145A with intonations of Greyed-Red Group 178B. Texture: Smooth.

Flower bud development: Flower buds are borne in corymbs of 3 to 11 flower buds per stem.

Flower bloom:

*Fragrance.*—Light rose scent.

*Duration.*—The blooms have a duration on the plant of approximately 15 days. Petals fall cleanly away from plant after flowers have fully matured.

*Size.*—Flower diameter is 50 mm when open. Flower depth is 22 mm.

*Flower shape.*—High centered, semi double, with a high pointed center which is tightly closed.

*Shape of flower, side view.*—The upper portion is convex. The lower portion is slightly concave.

Petalage: Under normal conditions, flowers have about 70 petals.

General tonality of flower: Open flowers are Red Group 46B.

Petal color:

*Upon opening, outer petals.*—Upper surface: Red Group 46B. Lower surface: Red Group 53C.

*Upon opening, inner petals.*—Upper surface: Red Group 46B. Lower surface: Red Group 53C.

*Basal petal spots, upon opening.*—Upper surface: Yellow Group 8A. Lower surface: Yellow Group 8A.

*After opening, outer petals.*—Upper surface: Red Group 46B. Lower surface: Red Group 53C.

*After opening, inner petals.*—Upper surface: Red Group 46B. Lower surface: Red Group 53C.

*Basal petal spots, after opening.*—Upper surface: Yellow Group 8A. Lower surface: Yellow Group 8A.

Petals:

*Petal reflex.*—Strong.

*Margin.*—Entire and uniform.

*Shape.*—Generally broad and elliptical. Apex shape: Rounded. Base shape: Acute.

*Size.*—25 mm (l)×25 mm (w).

*Texture.*—Smooth.

*Thickness.*—Average.

Petaloids:

*Size.*—13 mm (l) by 9 mm (w).

*Quantity.*—About 5.

*Shape.*—Elliptic, with a rounded apex and acute base.

*Color.*—Upper surface is Red Group 46B with a petaloid spot of Yellow Group 8A. Lower surface is Red Group 53C with a petaloid spot of Yellow Group 8A.

Reproductive flower parts:

*Pollen.*—None observed.

*Anthers.*—Size: 1 mm in length. Color: Greyed-Yellow Group 161A. Quantity: 33 on average.

*Filaments.*—Color: Yellow Group 1D. Length: 3 mm.

*Pistils.*—Length: 5 mm. Quantity: 20 on average.

*Stigmas.*—Color: Greyed-Yellow Group 160C.

*Styles.*—Color: Green-White Group 157A.

*Location of stigmas.*—Level in location relative to the length of the filaments and the height of the anthers.

*Hips.*—None Observed.

PLANT

Plant growth: Upright, bushy. Plants are 30 cm in height, and 30 cm wide.

Stems:

*Color.*—Juvenile growth: Yellow-Green Group 144B with intonations of Greyed-Orange Group 177B and Greyed-Red Group 178A. Mature growth: Yellow-Green Group 144A with intonations of Greyed-Orange Group 177B and Greyed-Red Group 178A.

*Length.*—On average, canes are 13 cm from the base of the plant to the flowering portion.

*Diameter.*—About 5 mm.

*Internodes.*—On mature canes about 32 mm between nodes.

*Surface texture.*—Young wood: Smooth. Older wood: Smooth.

Long prickles:

*Incidence.*—3 prickles per 10 cm of stem.

*Size.*—Average length of prickles on mature stems is 3 mm.

*Shape.*—Upper portion is linear. Lower portion is concave.

*Color.*—Juvenile prickles: Greyed-Red Group 179A. Mature prickles: Greyed-Red Group 179A.

Plant foliage:

*Compound leaf.*—95 mm (l)×75 (w).

*Quantity.*—2 or 3 leaves per 10 cm of stem on average.

*Leaf bearing angle to the stem.*—45 degrees.

*Color of juvenile foliage.*—Upper side: Yellow-Green Group 146A with intonations of Greyed-Purple Group 183B. Lower side: Yellow-Green Group 144A.

*Color of mature foliage.*—Upper side: Yellow-Green Group 146A. Lower side: Yellow-Green Group 146B.

Plant leaves and leaflets:

*Stipules.*—Size: 18 mm long, 3 mm wide. Quantity: 2 per compound leaf. Shape: Linear, slightly broad based with outward extending apices. Margins: Finely serrated. Color: Yellow-Green Group 144A.

*Petiole.*—Length: 25 mm. Diameter: 2 mm.

*Upper surface.*—Color: Yellow-Green Group 144A with intonations of Greyed-Purple Group 183B.

*Lower surface.*—Color: Yellow-Green Group 144A.

*Rachis.*—Length: About 35 mm. Diameter: About 1.5 mm. Upper surface: Color: Yellow-Green Group 144A with intonations of Greyed-Purple Group 183B.

*Lower surface.*—Color: Yellow-Green Group 144A.

*Leaflet.*—Quantity: Normally 5 leaflets. Margins: Serrated. Size: On average terminal leaflets are 42 mm long, 25 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar100', substantially as illustrated and described herein, due to its abundant red flowers, disease resistance, and extended period of bloom.

* * * * *

'Poulpar100'

'Poulpar100'